(12) United States Patent
Frasier et al.

(10) Patent No.: US 7,955,257 B2
(45) Date of Patent: Jun. 7, 2011

(54) NON-RIGID SURGICAL RETRACTOR

(75) Inventors: William J. Frasier, New Bedford, MA (US); Timothy Beardsley, Kingston, MA (US); Connie P. Marchek, Foxboro, MA (US)

(73) Assignee: DePuy Spine, Inc., Raynham, MA (US)

( * ) Notice: Subject to any disclaimer, the term of this patent is extended or adjusted under 35 U.S.C. 154(b) by 283 days.

(21) Appl. No.: 11/540,780

(22) Filed: Sep. 29, 2006

(65) Prior Publication Data

US 2007/0156023 A1   Jul. 5, 2007

Related U.S. Application Data

(60) Provisional application No. 60/756,378, filed on Jan. 5, 2006.

(51) Int. Cl.
*A61B 1/32* (2006.01)
(52) U.S. Cl. .................. 600/206; 600/208; 600/233
(58) Field of Classification Search .............. 600/37, 600/184–246; 606/151
See application file for complete search history.

(56) References Cited

U.S. PATENT DOCUMENTS

| | | | |
|---|---|---|---|
| 447,761 A | 3/1891 | Clough | |
| 475,975 A | 3/1892 | Clough | |
| 2,053,868 A | 9/1936 | Grosso | |
| 2,320,709 A | 6/1943 | Arnesen | |
| 3,246,646 A | 4/1966 | Murphy | |
| 3,486,505 A | 12/1969 | Morrison | |
| 3,522,799 A | 8/1970 | Gauthier | |
| 3,563,236 A | 2/1971 | Hansson | |
| 3,771,518 A | 11/1973 | Greissing et al. | |
| 3,848,601 A | 11/1974 | Ma et al. | |
| 3,965,890 A | 6/1976 | Gauthier | |
| 4,010,741 A | 3/1977 | Gauthier | |
| 4,130,113 A | 12/1978 | Graham | |

(Continued)

FOREIGN PATENT DOCUMENTS

EP       0428567 B1     5/1991

(Continued)

OTHER PUBLICATIONS

Mayer, H. Michael, "A New Microsurgical Technique for Minimally Invasive Anterior Lumbar Interbody Fusion," Spine, vol. 22(6):691-699 (1997).

*Primary Examiner* — Eduardo C Robert
*Assistant Examiner* — Christina Negrelli
(74) *Attorney, Agent, or Firm* — Nelson Mullins Riley & Scarborough LLP; Kevin J. Canning; EuiHoon Lee (57) ABSTRACT

The present invention provides a non-rigid retractor for providing access to a surgical site, such as a patient's spine, during a surgical process. When used in spinal surgery, the non-rigid retractor allows a surgeon to operate on one or more spinal levels. The non-rigid retractor includes at least one flexible strap anchored at a first end to the spine or other internal body part at the surgical site. The body of the at least one flexible strap extends from a skin incision and is anchored at a second location external to the body to retract skin and muscle from the surgical site, allowing adequate visualization of the surgical site and providing access for implants and surgical instruments to pass through the retractor and into the surgical site.

18 Claims, 7 Drawing Sheets

U.S. PATENT DOCUMENTS

| | | | |
|---|---|---|---|
| 4,156,424 A | 5/1979 | Burgin | |
| 4,254,763 A * | 3/1981 | McCready et al. | 600/230 |
| 4,263,899 A | 4/1981 | Burgin | |
| 4,274,398 A * | 6/1981 | Scott, Jr. | 600/233 |
| 4,421,107 A | 12/1983 | Estes et al. | |
| 4,434,791 A | 3/1984 | Darnell | |
| 4,545,374 A | 10/1985 | Jacobson | |
| 4,562,832 A | 1/1986 | Wilder et al. | |
| 4,573,448 A | 3/1986 | Kambin | |
| 4,686,966 A | 8/1987 | Tsai | |
| 4,765,311 A | 8/1988 | Kulik et al. | |
| 4,817,587 A | 4/1989 | Janese | |
| 4,862,891 A | 9/1989 | Smith | |
| 4,872,451 A | 10/1989 | Moore et al. | |
| 4,907,132 A | 3/1990 | Parker | |
| 4,934,352 A | 6/1990 | Sullivan, Jr. | |
| 5,000,163 A | 3/1991 | Ray et al. | |
| 5,052,372 A | 10/1991 | Shapiro | |
| 5,052,373 A | 10/1991 | Michelson | |
| 5,125,396 A | 6/1992 | Ray | |
| 5,135,525 A | 8/1992 | Biscoping et al. | |
| 5,158,543 A | 10/1992 | Lazarus | |
| 5,171,279 A | 12/1992 | Mathews | |
| 5,231,973 A | 8/1993 | Dickie | |
| 5,231,974 A | 8/1993 | Giglio et al. | |
| 5,242,443 A | 9/1993 | Kambin | |
| 5,279,567 A | 1/1994 | Ciaglia et al. | |
| 5,284,129 A | 2/1994 | Agbodoe et al. | |
| 5,292,309 A | 3/1994 | Van Tassel et al. | |
| 5,304,183 A | 4/1994 | Gourlay et al. | |
| 5,312,360 A | 5/1994 | Behl | |
| 5,342,384 A | 8/1994 | Sugarbaker | |
| 5,375,481 A | 12/1994 | Cabrera et al. | |
| 5,382,139 A | 1/1995 | Kawaguchi et al. | |
| 5,400,774 A | 3/1995 | Villalta et al. | |
| 5,415,666 A | 5/1995 | Gourlay et al. | |
| 5,429,121 A | 7/1995 | Gadelius | |
| 5,439,464 A | 8/1995 | Shapiro | |
| 5,472,426 A | 12/1995 | Bonati et al. | |
| 5,493,464 A | 2/1996 | Koshikawa | |
| 5,503,617 A | 4/1996 | Jako | |
| 5,509,893 A | 4/1996 | Pracas | |
| 5,520,610 A | 5/1996 | Giglio et al. | |
| 5,554,101 A | 9/1996 | Matula et al. | |
| 5,569,248 A | 10/1996 | Mathews | |
| 5,667,481 A | 9/1997 | Villalta et al. | |
| 5,681,265 A | 10/1997 | Maeda et al. | |
| 5,702,177 A | 12/1997 | Lin | |
| 5,728,046 A | 3/1998 | Mayer et al. | |
| 5,728,097 A | 3/1998 | Mathews | |
| 5,746,720 A | 5/1998 | Stouder, Jr. | |
| 5,755,660 A | 5/1998 | Tyagi | |
| 5,762,629 A | 6/1998 | Kambin | |
| 5,769,782 A | 6/1998 | Phan | |
| 5,779,629 A | 7/1998 | Hohlen | |
| 5,792,044 A | 8/1998 | Foley et al. | |
| 5,810,721 A | 9/1998 | Mueller et al. | |
| 5,813,978 A | 9/1998 | Jako | |
| 5,816,257 A | 10/1998 | Chin | |
| 5,875,782 A | 3/1999 | Ferrari et al. | |
| 5,879,291 A | 3/1999 | Kolata et al. | |
| 5,882,344 A | 3/1999 | Stouder, Jr. | |
| 5,891,147 A | 4/1999 | Moskovitz et al. | |
| 5,893,831 A | 4/1999 | Koros et al. | |
| 5,897,490 A | 4/1999 | Fox et al. | |
| 5,899,901 A | 5/1999 | Middleton | |
| 5,902,231 A | 5/1999 | Foley et al. | |
| 5,902,233 A | 5/1999 | Farley et al. | |
| 5,902,315 A | 5/1999 | DuBois | |
| 5,928,139 A * | 7/1999 | Koros et al. | 600/205 |
| 5,931,777 A | 8/1999 | Sava | |
| 5,944,658 A | 8/1999 | Koros et al. | |
| 5,947,896 A | 9/1999 | Sherts et al. | |
| 5,951,467 A * | 9/1999 | Picha et al. | 600/233 |
| 5,954,635 A | 9/1999 | Foley et al. | |
| 5,967,970 A | 10/1999 | Cowan et al. | |
| 5,967,972 A | 10/1999 | Santilli et al. | |
| 5,967,973 A | 10/1999 | Sherts et al. | |
| 5,968,098 A | 10/1999 | Winslow | |
| 5,976,146 A | 11/1999 | Ogawa et al. | |
| 5,981,147 A | 11/1999 | Hallock et al. | |
| 5,984,867 A * | 11/1999 | Deckman et al. | 600/232 |
| 6,030,340 A | 2/2000 | Maffei et al. | |
| 6,033,406 A | 3/2000 | Mathews | |
| 6,042,542 A | 3/2000 | Koros et al. | |
| 6,048,309 A * | 4/2000 | Flom et al. | 600/234 |
| 6,063,088 A | 5/2000 | Winslow | |
| 6,074,343 A | 6/2000 | Nathanson et al. | |
| 6,083,154 A | 7/2000 | Liu et al. | |
| 6,090,043 A * | 7/2000 | Austin et al. | 600/217 |
| 6,090,113 A | 7/2000 | Le Couedic et al. | |
| 6,120,434 A | 9/2000 | Kimura et al. | |
| 6,139,493 A | 10/2000 | Koros et al. | |
| 6,142,935 A | 11/2000 | Flom et al. | |
| 6,152,871 A | 11/2000 | Foley et al. | |
| 6,159,179 A | 12/2000 | Simonson | |
| 6,162,170 A | 12/2000 | Foley et al. | |
| 6,176,823 B1 | 1/2001 | Foley et al. | |
| 6,187,000 B1 | 2/2001 | Davison et al. | |
| 6,197,002 B1 | 3/2001 | Peterson | |
| 6,200,263 B1 | 3/2001 | Person | |
| 6,206,822 B1 | 3/2001 | Foley et al. | |
| 6,206,862 B1 | 3/2001 | Giamanco et al. | |
| 6,217,509 B1 | 4/2001 | Foley et al. | |
| 6,224,545 B1 | 5/2001 | Cocchia et al. | |
| 6,224,608 B1 | 5/2001 | Ciccolella et al. | |
| 6,241,659 B1 | 6/2001 | Bookwalter et al. | |
| 6,261,295 B1 | 7/2001 | Nicholson et al. | |
| 6,264,650 B1 | 7/2001 | Hovda et al. | |
| 6,267,763 B1 | 7/2001 | Castro | |
| 6,277,094 B1 | 8/2001 | Schendel | |
| 6,293,950 B1 * | 9/2001 | Lynch et al. | 606/77 |
| 6,306,170 B2 | 10/2001 | Ray | |
| 6,322,500 B1 | 11/2001 | Sikora et al. | |
| 6,331,157 B2 | 12/2001 | Hancock | |
| 6,342,036 B1 | 1/2002 | Cooper et al. | |
| 6,371,959 B1 | 4/2002 | Trice | |
| 6,371,968 B1 | 4/2002 | Kogasaka et al. | |
| 6,395,007 B1 | 5/2002 | Bhatnagar et al. | |
| 6,416,465 B2 | 7/2002 | Brau | |
| 6,416,468 B2 | 7/2002 | Deckman et al. | |
| 6,427,034 B1 | 7/2002 | Meis et al. | |
| 6,431,025 B1 | 8/2002 | Koros et al. | |
| 6,461,330 B1 | 10/2002 | Miyagi | |
| 6,464,634 B1 | 10/2002 | Fraser | |
| 6,468,207 B1 | 10/2002 | Fowler, Jr. | |
| 6,520,907 B1 | 2/2003 | Foley et al. | |
| 6,527,466 B1 | 3/2003 | Blier et al. | |
| 6,530,880 B2 | 3/2003 | Pagliuca | |
| 6,530,883 B2 | 3/2003 | Bookwalter et al. | |
| 6,530,926 B1 | 3/2003 | Davison | |
| 6,537,212 B2 | 3/2003 | Sherts et al. | |
| 6,592,582 B2 | 7/2003 | Hess et al. | |
| 6,599,292 B1 | 7/2003 | Ray | |
| 6,616,605 B2 | 9/2003 | Wright et al. | |
| 6,639,965 B1 | 10/2003 | Hsieh et al. | |
| 6,656,176 B2 | 12/2003 | Hess et al. | |
| 6,659,945 B2 | 12/2003 | Ball et al. | |
| 6,661,605 B1 | 12/2003 | Pust et al. | |
| 6,679,833 B2 | 1/2004 | Smith et al. | |
| 6,689,054 B2 | 2/2004 | Furnish et al. | |
| 6,692,434 B2 | 2/2004 | Ritland | |
| 6,712,825 B2 | 3/2004 | Aebi et al. | |
| 6,716,218 B2 | 4/2004 | Holmes et al. | |
| 6,723,043 B2 | 4/2004 | Kleeman et al. | |
| 6,729,205 B2 | 5/2004 | Phillips | |
| 6,733,445 B2 | 5/2004 | Sherts et al. | |
| 6,740,102 B2 | 5/2004 | Hess et al. | |
| 6,755,839 B2 | 6/2004 | Van Hoeck et al. | |
| 6,764,444 B2 | 7/2004 | Wu et al. | |
| 6,793,656 B1 | 9/2004 | Mathews | |
| 6,814,700 B1 | 11/2004 | Mueller et al. | |
| 6,869,398 B2 | 3/2005 | Obenchain et al. | |
| 6,893,394 B2 | 5/2005 | Douglas et al. | |
| 6,896,680 B2 | 5/2005 | Michelson | |
| 6,929,606 B2 | 8/2005 | Ritland | |
| 6,939,297 B2 | 9/2005 | Gannoe et al. | |

| | | |
|---|---|---|
| 6,945,933 B2 | 9/2005 | Branch et al. |
| 6,951,538 B2 | 10/2005 | Ritland |
| 6,982,740 B2 | 1/2006 | Adair et al. |
| 7,008,432 B2 | 3/2006 | Schlapfer et al. |
| 7,052,497 B2 | 5/2006 | Sherman et al. |
| 7,074,226 B2 | 7/2006 | Roehm, III et al. |
| 7,081,118 B2 | 7/2006 | Weber et al. |
| 7,087,055 B2 | 8/2006 | Lim et al. |
| 7,097,647 B2 | 8/2006 | Segler |
| 7,150,714 B2 | 12/2006 | Myles |
| 7,156,085 B2 | 1/2007 | Lewis et al. |
| 7,179,225 B2 | 2/2007 | Shluzas et al. |
| 7,179,261 B2 | 2/2007 | Sicvol et al. |
| 7,198,598 B2 | 4/2007 | Smith et al. |
| 7,207,949 B2 | 4/2007 | Miles et al. |
| 7,223,233 B2 | 5/2007 | Branch et al. |
| 7,250,052 B2 | 7/2007 | Landry et al. |
| 7,261,688 B2 | 8/2007 | Smith et al. |
| 7,264,589 B2 | 9/2007 | Sharratt |
| 7,491,168 B2 | 2/2009 | Raymond et al. |
| 7,556,601 B2 | 7/2009 | Branch et al. |
| 2001/0009971 A1 | 7/2001 | Sherts et al. |
| 2001/0029377 A1 | 10/2001 | Aebi et al. |
| 2002/0002324 A1* | 1/2002 | McManus ............... 600/208 |
| 2002/0022764 A1 | 2/2002 | Smith et al. |
| 2002/0058948 A1 | 5/2002 | Arlettaz |
| 2002/0080248 A1 | 6/2002 | Adair et al. |
| 2002/0143235 A1 | 10/2002 | Pagliuca |
| 2002/0193666 A1 | 12/2002 | Sherts et al. |
| 2003/0004401 A1* | 1/2003 | Ball et al. ............... 600/233 |
| 2003/0060687 A1 | 3/2003 | Kleeman et al. |
| 2003/0149341 A1 | 8/2003 | Clifton |
| 2003/0191371 A1 | 10/2003 | Smith et al. |
| 2003/0220650 A1 | 11/2003 | Major et al. |
| 2004/0034351 A1 | 2/2004 | Sherman et al. |
| 2004/0087833 A1 | 5/2004 | Bauer et al. |
| 2004/0138662 A1 | 7/2004 | Landry et al. |
| 2004/0143167 A1 | 7/2004 | Branch et al. |
| 2004/0143169 A1 | 7/2004 | Branch et al. |
| 2004/0230191 A1 | 11/2004 | Frey et al. |
| 2004/0242969 A1 | 12/2004 | Sherts et al. |
| 2005/0043592 A1 | 2/2005 | Boyd et al. |
| 2005/0131422 A1 | 6/2005 | Anderson et al. |
| 2005/0137461 A1 | 6/2005 | Marchek et al. |
| 2005/0159650 A1 | 7/2005 | Raymond et al. |
| 2005/0159651 A1 | 7/2005 | Raymond et al. |
| 2005/0171551 A1 | 8/2005 | Sukovich et al. |
| 2005/0215866 A1 | 9/2005 | Kim |
| 2005/0273133 A1 | 12/2005 | Shluzas et al. |
| 2006/0074278 A1 | 4/2006 | Petit et al. |
| 2006/0084844 A1 | 4/2006 | Nehls |
| 2006/0195017 A1 | 8/2006 | Shluzas et al. |
| 2006/0207612 A1* | 9/2006 | Jackson et al. ............... 128/860 |
| 2006/0224044 A1 | 10/2006 | Marchek et al. |
| 2006/0247651 A1 | 11/2006 | Roehm et al. |
| 2007/0038033 A1 | 2/2007 | Jones et al. |
| 2007/0060795 A1* | 3/2007 | Vayser et al. ............... 600/245 |
| 2007/0106123 A1* | 5/2007 | Gorek et al. ............... 600/210 |
| 2007/0156023 A1 | 7/2007 | Frasier et al. |
| 2007/0156024 A1 | 7/2007 | Frasier et al. |
| 2007/0156025 A1 | 7/2007 | Marchek et al. |
| 2007/0156026 A1 | 7/2007 | Frasier et al. |
| 2007/0208228 A1 | 9/2007 | Pavento et al. |
| 2008/0021285 A1 | 1/2008 | Drzyzga et al. |
| 2009/0018399 A1 | 1/2009 | Martinelli et al. |

FOREIGN PATENT DOCUMENTS

| | | |
|---|---|---|
| EP | 0908140 A1 | 4/1999 |
| EP | 0931509 A1 | 7/1999 |
| EP | 1090586 A2 | 4/2001 |
| EP | 1090589 A1 | 4/2001 |
| EP | 1192905 A1 | 4/2002 |
| EP | 1195141 A2 | 4/2002 |
| FR | 2807313 A1 | 10/2001 |
| JP | 2-198764 | 8/1990 |
| WO | 90/01298 A1 | 2/1990 |
| WO | 96/02195 A1 | 2/1996 |
| WO | 0698374 A2 | 2/1996 |
| WO | 98/17208 A2 | 4/1998 |
| WO | 00/18306 A1 | 4/2000 |
| WO | 01/80725 A1 | 11/2001 |
| WO | 02/060330 A1 | 8/2002 |
| WO | 03/000140 A1 | 12/2003 |
| WO | 2005/096735 A2 | 10/2005 |

* cited by examiner

NON-RIGID SURGICAL RETRACTOR

RELATED APPLICATION

This application claims the benefit of U.S. Patent Application Ser. No. 60/756,378, filed Jan. 5, 2006, the contents of which are hereby incorporated by reference.

FIELD OF THE INVENTION

The present invention relates to a device and method for accessing a surgical site during surgery, such as spinal surgery. More particularly, the present invention relates to a device and method for retracting tissue surrounding a surgical site during a surgery.

BACKGROUND OF THE INVENTION

Spinal retraction systems are used in spinal surgery to provide access to a patient's spine by retracting and holding back tissue from a targeted surgical site beneath the skin. Current spinal retraction systems are rigid and therefore have difficulty conforming to patient anatomy. The rigid nature of such spinal retraction systems may also lead to increased danger to skin, nerves, vessels or muscle tissue, and often an inability to get good muscle retraction at a desired location. In addition, rigid retractors require a bed-mounted arm to hold the retractor in place relative to the patient's body.

SUMMARY OF THE INVENTION

The present invention provides a non-rigid retractor for providing access to a surgical site, such as a patient's spine, during a surgical process. When used in spinal surgery, the non-rigid retractor allows a surgeon to operate on one or more spinal levels. The non-rigid retractor includes at least one flexible strap anchored at a first end to the spine or other internal body part at the surgical site. The body of the at least one flexible strap extends from a skin incision and is anchored at a second location external to the body to retract skin and muscle from the surgical site, allowing adequate visualization of the surgical site and providing access for implants and surgical instruments to pass through the retractor and into the surgical site.

In accordance with a first aspect of the present invention, a non-rigid retractor for retracting tissues in an incision for a surgical site is provided. The non-rigid retractor comprises a flexible strap formed at least partially of a biocompatible material and a first anchor for anchoring a first portion of the flexible strap to a body part within the incision.

In certain embodiments, the non-rigid surgical retractor may comprise a plurality of flexible straps anchored to and extending about the periphery of the surgical incision.

In accordance with another aspect of the present invention, a method is provided for providing access to a surgical site in a patient. The method comprises the steps of attaching an anchor on a distal end of a flexible strap formed of a biocompatible material to a bone in the surgical site through an incision; and pulling a proximal end of the flexible strap out of the incision.

In accordance with another aspect, an anchoring device is provided for anchoring one or more flexible straps external to the incision. The anchoring device may comprise a ring having a central opening for surrounding the incision and anchoring means distributed on the periphery of the ring. Each anchoring means is configured to receive and retain a portion of a flexible strap anchored at one end to an internal location within an incision accessing a surgical site.

BRIEF DESCRIPTION OF THE FIGURES

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DETAILED DESCRIPTION OF THE INVENTION

The present invention provides an improved surgical device and method for retracting tissue from an incision and providing access to a surgical site in a patient. The present invention will be described below relative to certain exemplary embodiments in spinal surgery to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein. For example, while the illustrative embodiment of the invention relates to a spinal retractor used in spinal surgery, the non-rigid surgical retractor may be used in any surgical process where access to a surgical site is required.

Figure 1:
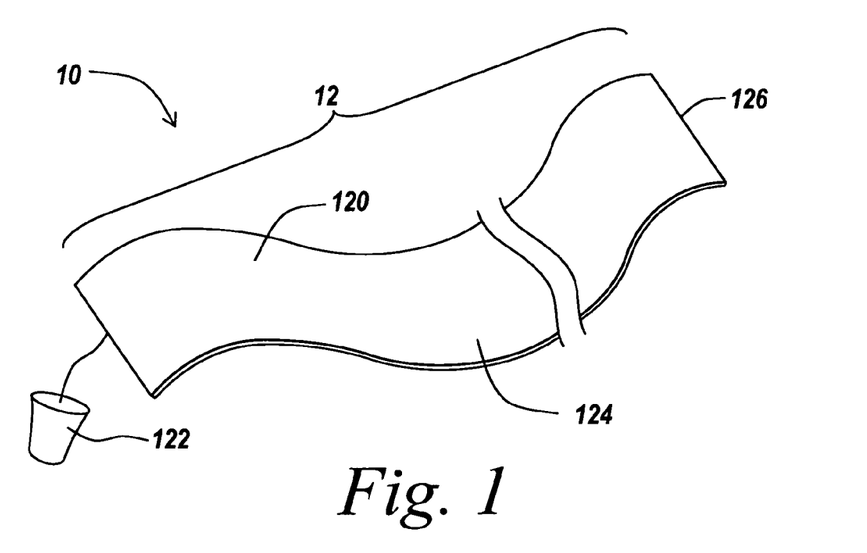
FIG. 1 illustrates an embodiment of a non-rigid surgical retractor of an illustrative embodiment of the invention.

FIG. 1 illustrates an embodiment of a non-rigid surgical retractor 10 of an illustrative embodiment of the invention. The illustrative surgical retractor 10 comprises at least one flexible strap 12 formed of a flexible, biocompatible material. The flexible strap 12 includes a first end 120 that is anchored to the spine, for example, a vertebra, or other body part in a surgical site via a bone anchor 122. When implanted in an incision in the skin for accessing a surgical site, the body of the flexible strap 124 extends out of the incision, and a second portion of the flexible strap, such as the second end 126, anchors to a selected location external to the incision. When implanted, the flexible body 124 retracts and retains the tissue surrounding the anchored portion of the surgical site to provide access for instruments and surgical implants to the surgical site.

Figure 2:
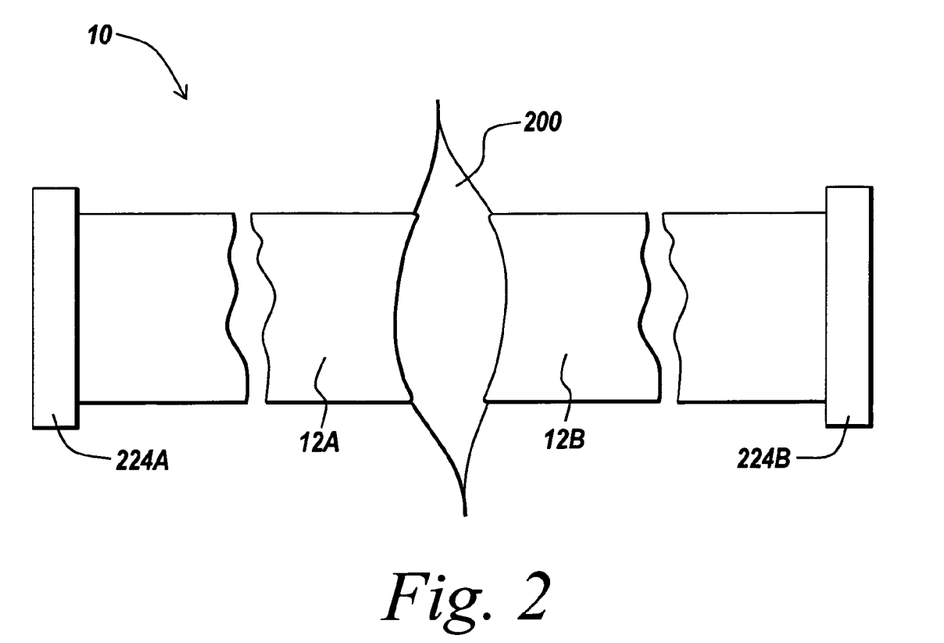
FIG. 2 illustrates an embodiment of a non-rigid surgical retractor including a plurality of flexible straps according to an illustrative embodiment of the invention.

The non-rigid surgical retractor 10 may comprise any suitable number of flexible straps 12. For example, the embodiment of FIG. 2, the non-rigid surgical retractor 10 comprises a pair of flexible straps 12A and 12B anchored to a surgical site and extending external to an incision 200 in a patient's skin for accessing the surgical site. As shown in FIG. 2, each flexible strap 12A and 12B is pulled against the tissue to retract the tissue in the incision 200. External anchors 224A and 224B anchor the straps 12A, 12B external to the incision to hold the tissue in the retracted position.

Alternatively, the non-rigid surgical retractor 10 comprises a single flexible strap, as shown in FIG. 1, or several flexible straps that are distributed about the periphery of the incision for accessing the surgical site. Different sized and shaped straps can be used to limit tissue creep during retraction.

The material forming the body 124 of the flexible strap may comprise any suitable biocompatible material suitable for retracting tissue. Examples of suitable materials include, but are not limited to: wool, silk, cotton, linen, hemp, ramie, jute, acetate, acrylic, lastex, nylon, polyester, rayon, spandex, carbon fiber, fiberglass, including PTFE-coated fiberglass and silicon-coated fiberglass, Kevlar, Teflon, ceramic, carbon, graphite, rubber, Polyglycolic Acid (PGA), Poly 1-Lactid Acid (PLA), PTFE, stainless steel, aluminum, titanium, and combinations thereof. In some embodiments the flexible straps may be formed of a radiolucent material or resorbable material.

In some embodiments an illuminant can be coupled to the flexible strap to provide illumination at the incision site. In one example, the illuminant may be a luminescent chemical coupled to the flexible straps. In one such embodiment, the strap itself is treated with a luminescent chemical. In another such embodiment, a luminescent chemical is provided in tubing attached to the straps. In another example, fiber optics attached to or embedded in the straps may be used to provide illumination at the incision site.

In certain embodiments the flexible straps may be coated with therapeutic agents allowing the flexible straps to be used for drug delivery at the surgical site. For example, pain medication, antibiotics, anti-inflammatories, and other medications may be applied to the flexible straps and delivered at the incision site by the flexible strap. Additionally, the straps may contain adhesives to promote wound closure.

Other possible sizes, shapes, materials, and configurations will be apparent to one skilled in the art given the benefit of this disclosure.

The bone anchor 122 for attaching the flexible strap 12 to a bone or other body part may comprise any suitable device for anchoring the flexible strap to a body part such as a screw, pin, or the like. For example, in one embodiment, the bone anchor 122 comprises a resorbable anchor. Alternatively the bone anchor 122 may comprise a biocompatible anchor formed of a non-resorbable material. The anchor 122 may attach directly to the bone or body part. Alternatively, an intermediate anchor, such as pedicle screws fixed to pedicle bone in the spine, may be used to connect a flexible strap 12 to the body part.

The second portion 126 of the flexible strap 12 may be anchored external to the incision using any suitable means. Examples of suitable external anchoring mechanisms include, but are not limited to, Velcro, adhesive, tape, clips, snaps or other suitable anchoring means known in the art. Other possible anchoring mechanisms will be apparent to one skilled in the art given the benefit of this disclosure.

Figure 3:
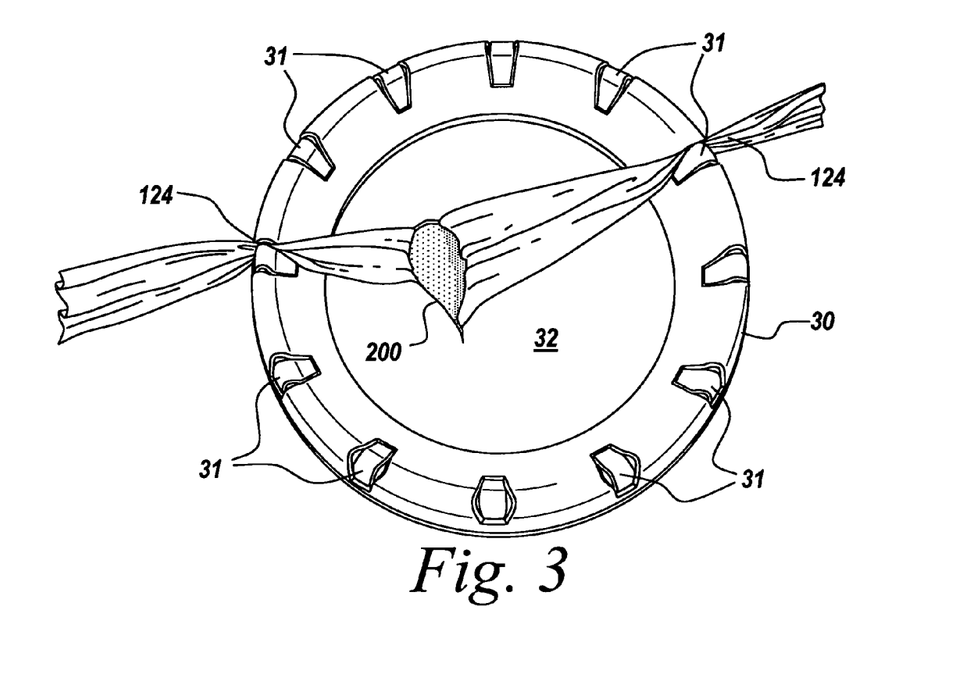
FIG. 3 illustrates an embodiment of a non-rigid surgical retractor including a plurality of flexible straps anchored using an anchoring ring according to an illustrative embodiment of the invention.

In one embodiment of the invention, shown in FIG. 3, the external anchoring mechanism may comprise a ring 30 configured to rest on the skin, surrounding the incision site 200 and having a plurality of external anchoring mechanisms 31 distributed about the periphery of the ring for receiving a second portion 126 of the flexible strap(s) 12. A central opening 32 in the ring 30 provides access to the incision site 200. The anchoring ring 30 may have any suitable shape, size and configuration and is not limited to a round shape. Additional shapes such as triangles, rectangles, or other geometries are possible.

Figure 4:
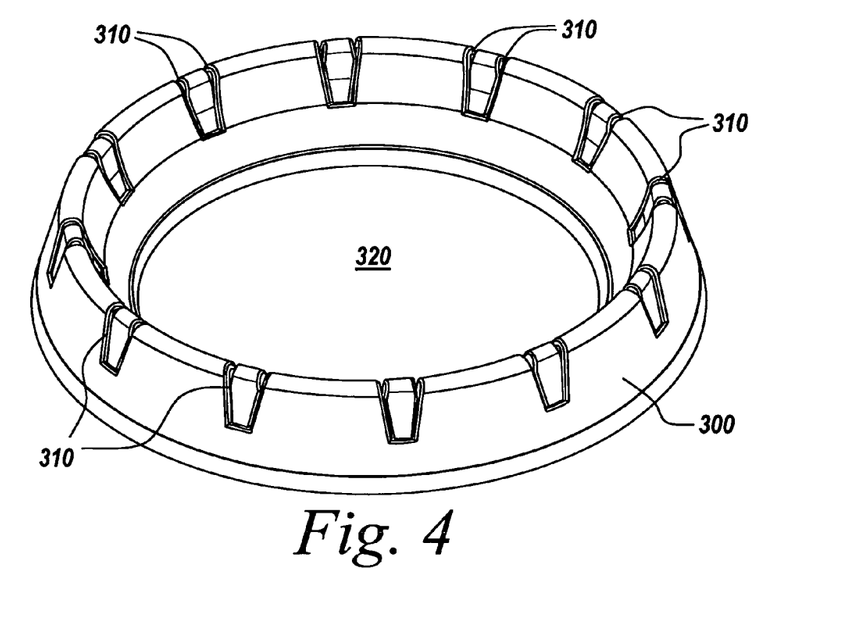
FIG. 4 illustrates an embodiment of an anchoring ring.

The ring 30 may have any configuration suitable for anchoring one or more flexible retraction straps while providing access to the surgical site. For example, as shown in FIG. 4, an anchoring ring 300 for a retraction strap may comprise a plurality of peripheral slots 310 about a central opening 320 for receiving and retaining a portion of a retraction strap by friction fit. This configuration allows control over retraction force as the surgeon can pull the retraction strap to retract tissue farther back, or loosen the strap to release the tissue.

Figure 5:
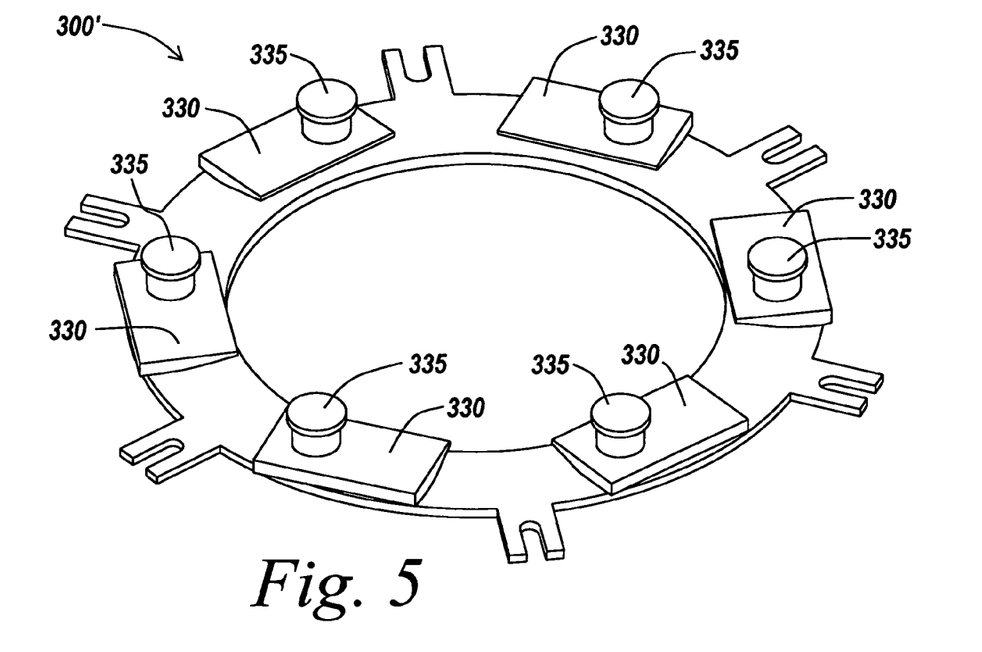
FIG. 5 illustrates another embodiment of an anchoring ring.

According to another embodiment, an anchoring ring 300', shown in FIG. 5, may comprise a plurality of clamps distributed about a peripheral opening. In this example, the clamps 330 can be screwed down, here using thumb screws 335, to secure the retraction strap to the anchoring ring 300'. In other embodiments, the clamps may be spring loaded. In some embodiments, the clamping mechanism may include a ratcheting mechanism. The retracting strap could be placed into the ratcheting mechanism and tightened thereby retracting the tissue. The ratcheting mechanism maintains tension on the retracting strap while allowing for further tightening and thus retraction of tissue.

Figure 6:
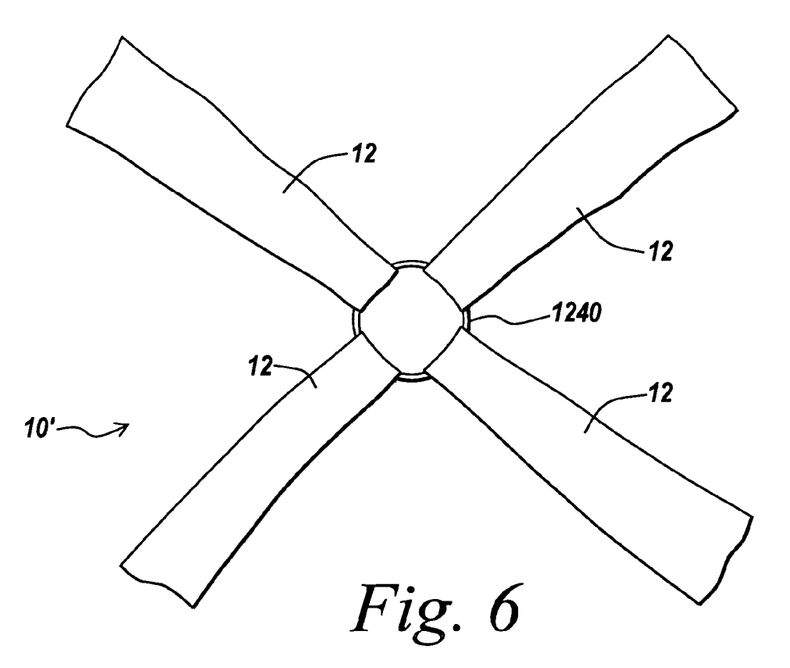
FIG. 6 illustrates an embodiment of a non-rigid surgical retractor including a plurality of flexible straps connected distally to a ring according to an illustrative embodiment of the invention.

According to another embodiment of the invention, a non-rigid surgical retractor 10' can comprise a distal connection member 1240, here a ring, having one or more flexible straps 12 attached thereto, as shown in FIG. 6. The flexible straps 12 may be permanently or removably attached to the distal connection member 1240. The distal connection member 1240 is fixed to a body part at a surgical site, such as the spine, with anchors, such as pins, screws, clips, staples, resorbable fixation devices, and other anchoring means known in the art. Alternately, the distal connection member 1240 may be deformed to fit around the spinal anatomy, like a rubber band, using no anchors but the tension of the ring. The distal connection member 1240 is preferably deformable to facilitate insertion of the retractor into the incision. The member 1240 may deform from an initial configuration to a collapsed configuration, whereupon release it may return to the initial configuration. The member 1240 may be formed of any suitable material, such as, but not limited to, rubber, plastic and flexible metal. The distal connection member 1240 may have any suitable shape and is not limited to a round shape. When the distal connection member 1240 is attached to a body part at a surgical site, the flexible straps extend from an incision for accessing the surgical site and are used to hold back the soft tissue within the incision. The flexible straps 12 may be anchored external to the incision using any suitable external anchoring means.

Figure 7:
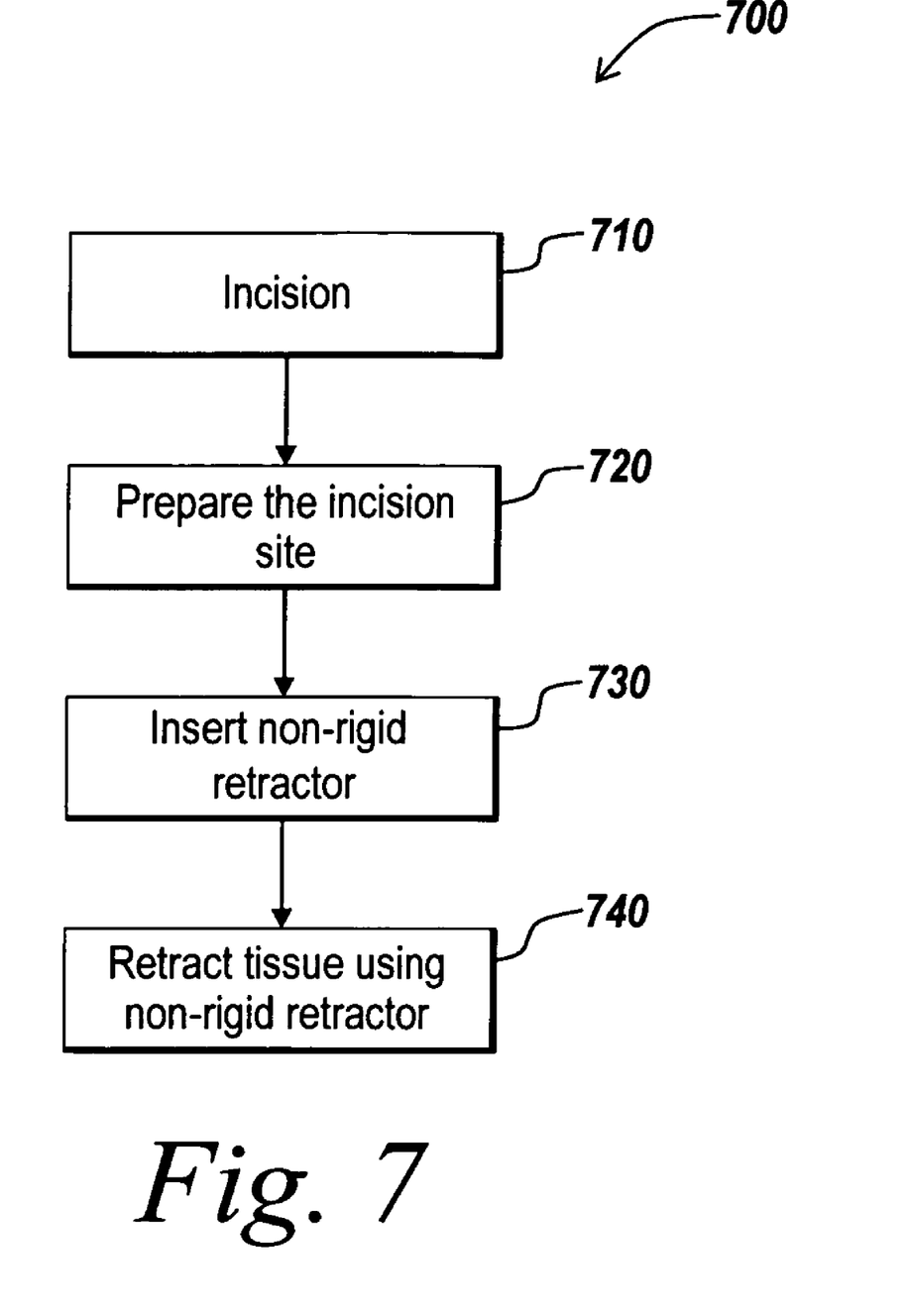
FIG. 7 illustrates a flow diagram for an exemplary embodiment of a method of using a non-rigid retractor of the invention.

FIG. 7 is a flow diagram 700 for one exemplary method of providing access to a surgical site in a patient using a non-rigid retractor. First, an incision is made at the surgical site 710. The incision site may then be prepared for the insertion of the non-rigid retractor 720. The non-rigid retractor can then be inserted into the incision site 730. Once inserted, the non-rigid retractor can then be used to retract tissue from the surgical site 740.

Figure 8A:
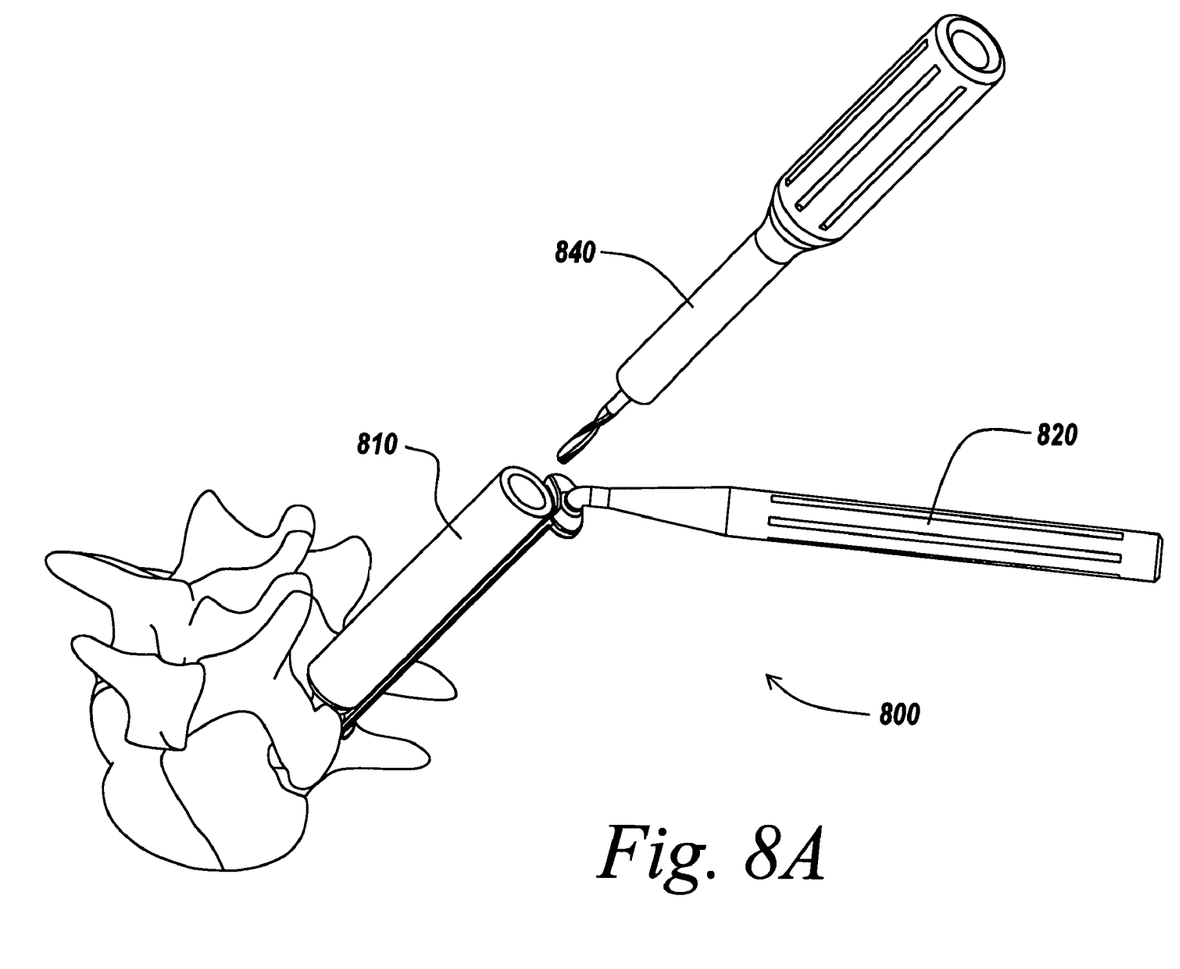
FIG. 8A illustrates an embodiment of a retractor/guide and drill used in installing a non-rigid retractor of the invention.

In one embodiment, the step of preparing the incision (step 720) involves additional steps. For example, blunt finger dissection between muscle planes may be performed. Continuous or serial dilation with or without a guide wire may be performed to expand the incision opening for insertion of a guide or retractor. Then a guide or retractor can be inserted into the incision. The guide or retractor can be used to sweep back muscle and tissue from the surgical site to find a target for attaching a flexible strap formed of a biocompatible material. An example of suitable retractor/guide can be seen in FIG. 8A. Here the retractor/guide 800 features a hollow insertion cannula 810 for guiding the insertion and removal of surgical instruments, including the non-rigid retractor, and a handle 820 attached to the proximal end of the cannula 810 for inserting and positioning the insertion cannula 810 in the incision site. Once a target for attaching a flexible strap is located a drill 840 or awl may be used to create an anchor hole for attaching the flexible strap. Examples of suitable targets include portions of a vertebra, such as a pedicle, vertebral body, spinous process, transverse process, lamina, facet or the like. In certain embodiments intermediate anchors such as pedicle screws can be used for attaching the flexible strap.

Figure 8B:
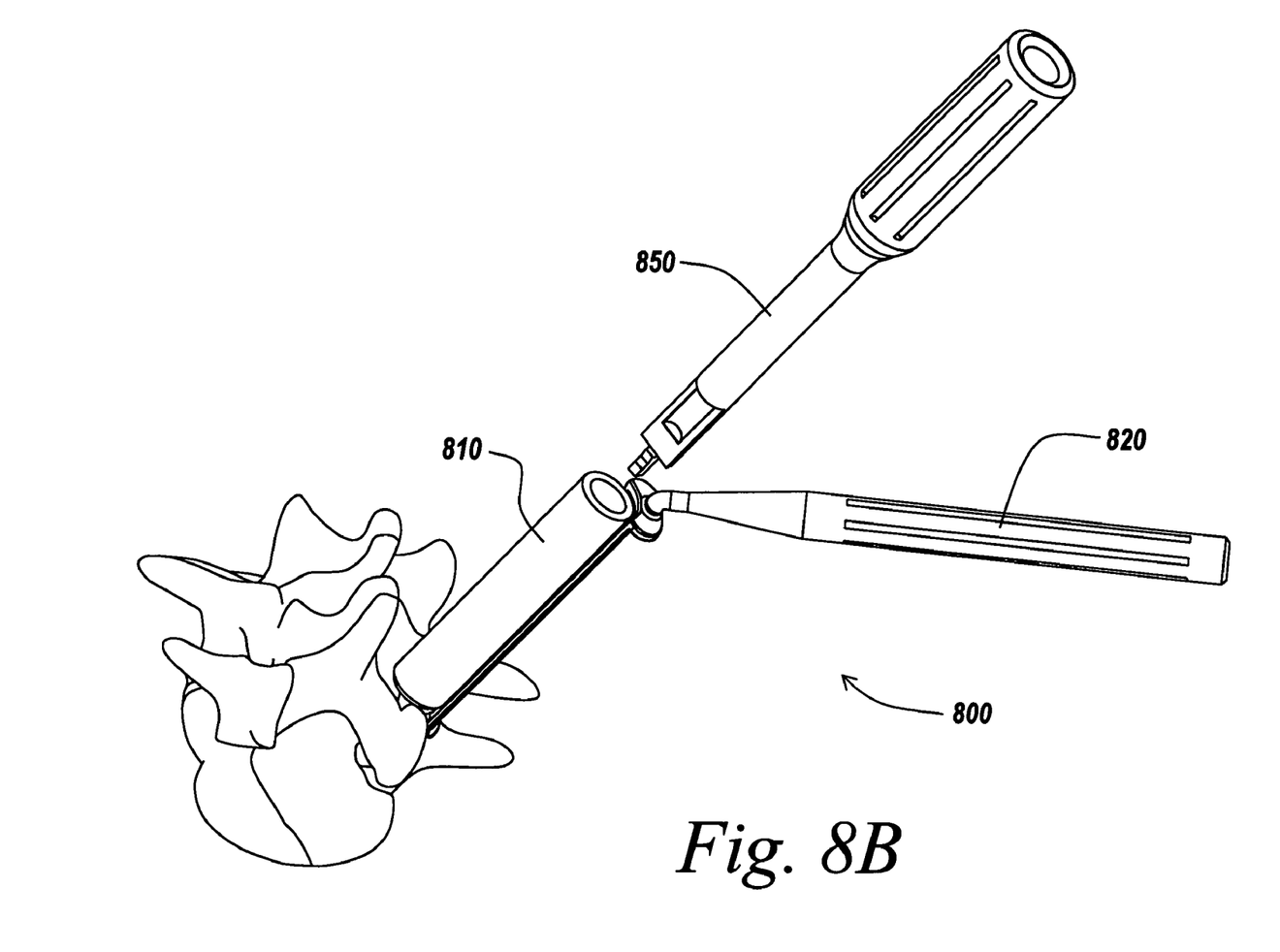
FIG. 8B illustrates an embodiment of an inserter tool used in installing a non-rigid retractor of the invention

Referring again to FIG. 7, the step of inserting the non-rigid retractor (step 730) may also involve multiple steps. In one example, these steps include attaching an anchor on a distal end of flexible strap formed of a biocompatible material to a bone in the surgical site through the incision and pulling a proximal end of the flexible strap out of the incision. In some embodiments this involves using the retractor/guide shown in FIG. 8A. In such an example, the hollow insertion cannula 820 of the retractor/guide 800 is inserted in the incision. An anchor of the flexible strap is passed through the hollow insertion cannula 820 such that the body of the flexible strap extends through a hollow opening in the hollow insertion cannula 820. The anchor of the flexible strap is then attached to the target. The hollow insertion cannula 820 of the retractor/guide 800 may then be withdrawn from the insertion so that the flexible strap extends from the incision. In some embodiments an insertion tool 850 as shown in FIG. 8B is used. The inserter tool 850 is used to pass the anchor of the flexible strap though the insertion cannula and attach the anchor to the target.

Figure 9A:
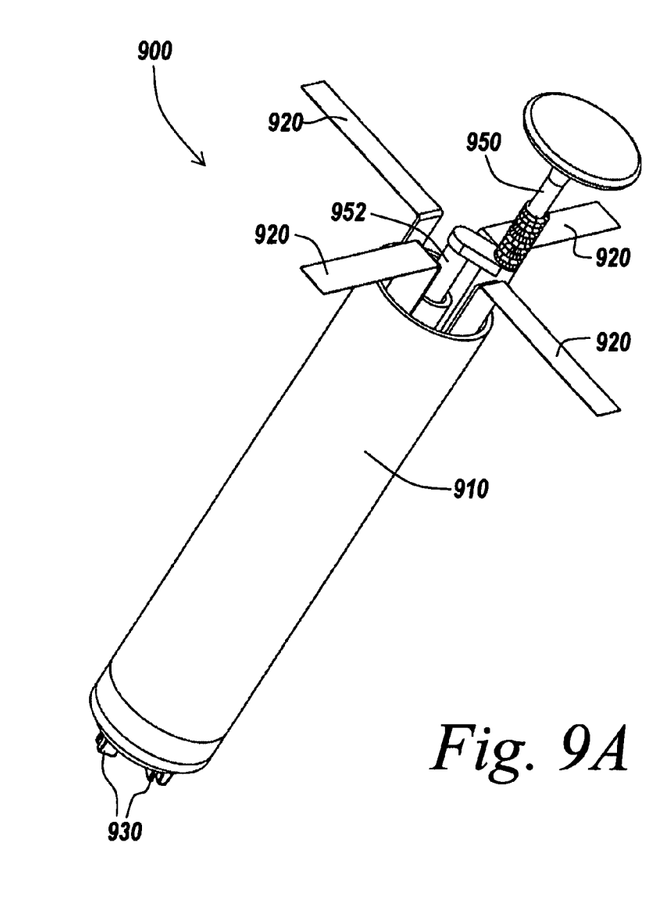
FIGS. 9A and 9B illustrate an embodiment of a system for inserting a non-rigid retractor of the invention.
Figure 9B:
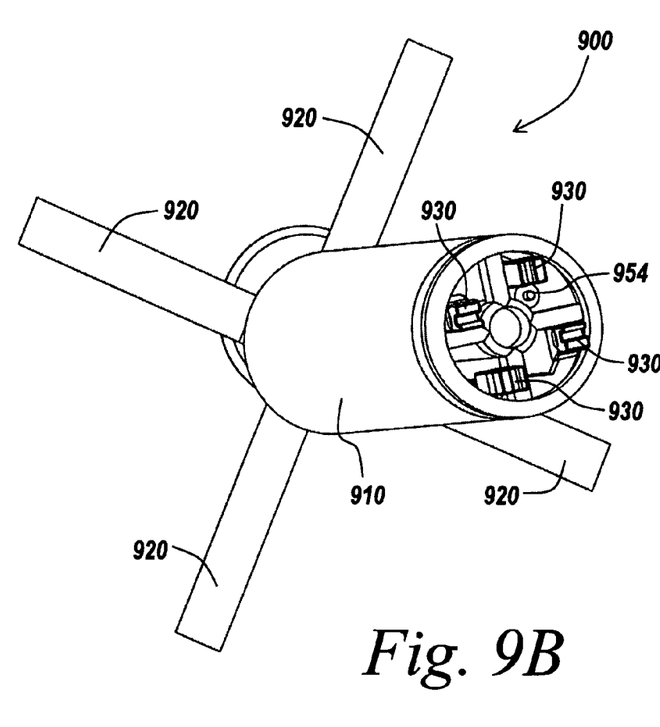

In another embodiment shown in FIGS. 9A and 9B, a system 900 is provided in which the guide, such as a cannula 910, is pre-loaded with a non-rigid retractor. In the example of FIGS. 9A and 9B the non-rigid retractor comprises four flexible straps 920 each with an anchor 930 for anchoring the respective flexible strap 920. It should be noted however that the non-rigid retractor may have any number of flexible straps as discussed with regard to embodiments above. With the non-rigid retractor preloaded in the cannula 910, the process of inserting the cannula 910 into the incision also serves to insert the non-rigid retractor. Once the system 900 is in position, the anchors 930 of the flexible straps 920 can be attached to the target. The cannula 910 of the system 900 may then be withdrawn from the insertion so that the flexible straps 920 extend from the incision.

In some embodiments an insertion tool is used to attach an anchor 930 to a target. In certain embodiments, the insertion tool may be part of the system 900. In the example of FIGS. 9A and 9B, the insertion tool 950 is a plunger-type mechanism mounted on a center spindle 952 allowing the insertion tool 950 to rotate so that the distal end 954 of the inserter tool 950 can engage the anchors 930 of the flexible straps 920 attaching the anchors 930 to the target using the plunger action of the insertion tool 950.

It should be understood that the examples of FIGS. 9A and 9B are but one of many possible examples of a system. Other possible guides, configurations, and insertion tools will be apparent to skilled in the art given the benefit of this disclosure.

Once the non-rigid retractor has been inserted, it can then be used to retract tissue at the surgical site (step 740). In some embodiments, this involves retracting tissue surrounding the incision using the flexible strap and anchoring the proximal end of the flexible strap external to the incision. In certain embodiments this can be performed using an anchoring ring. In one such example this involves placing an anchoring ring having a central opening for surrounding the incision site and anchoring portions distributed on the periphery of the ring for receiving the proximal end of the flexible strap externally over the incision. The proximal end of the flexible strap can then be secured in an anchoring portion distributed on the periphery of the ring. In other embodiments, the proximal end of the flexible strap may be secured without the use of an anchoring ring. For example, the proximal end may be self-adhesive allowing the proximal end to be secured to the patient, or the proximal end may be secured to the patient or drape using clips.

The process set forth in FIG. 7 and discussed above can then be repeated to place a number of flexible straps to retract tissue at a surgical site. Once sufficient retraction of the tissue is obtained, necessary surgical procedures may then be performed at the surgical site. After the procedure has been performed at the surgical site, one or more flexible straps may be disconnected and removed allowing the incision to be closed. As discussed above, many of the components of the non-rigid retractor, such as the anchor or strap, may be made of a bio-absorbable or biocompatible material such that components, like the anchors or straps, may be left in the body of the patient.

The apparatus and techniques of the present invention provide numerous advantages. The non-rigid retractor of the present invention can be used in any approach, including lateral, posterior, and anterior. The non-rigid retractor is highly adaptive, in that additional straps can be used for additional retraction. The flexible nature of the straps prevents damage to tissue, vessels, and muscle and alleviates the need for a bed-mounted arm to secure the retractor. The retractor may also be secured to an anchor ring or to the patient's skin which may eliminate the necessity of a bed mounted arm. The flexible nature of the straps allows the retractor to be easily adjusted to provide varying amounts of tension on the retracted tissue.

Although the present invention has been described relative to an illustrative embodiment and application in spinal correction surgery, it should be apparent that the present invention may be used in any number of surgical procedures. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A non-rigid retractor for retracting tissues in an incision for a surgical site, comprising:
a flexible strap formed at least partially of a biocompatible material;

a first bone anchor for anchoring a first portion of the flexible strap to a bone within the incision; and a second anchor for anchoring a second portion of the flexible strap at a location external to the incision site, wherein the first bone anchor comprises a resorbable anchor, and the second anchor comprises a ring having a central opening for surrounding the incision site and anchoring portions distributed on the periphery of the ring for receiving the second portion of the flexible strap.

2. The non-rigid retractor of claim 1, wherein the first bone anchor is formed at a first end of the flexible strap.

3. The non-rigid retractor of claim 1, wherein the ring includes at least one notch for receiving the second portion of the flexible strap.

4. The non-rigid retractor of claim 1, wherein the anchoring portions comprise clamps for clamping the second portion of the flexible strap.

5. The non-rigid retractor of claim 1, wherein the second anchor comprises a self adhesive anchor.

6. The non-rigid retractor of claim 1, wherein the biocompatible material comprises one of: wool, silk, cotton, linen, hemp, ramie, jute, acetate, acrylic, lastex, nylon, polyester, rayon, spandex, carbon fiber, fiberglass, Kevlar, Teflon, ceramic, carbon, graphite, rubber, Polyglycolic Acid (PGA), Poly 1-Lactid Acid (PLA), PTFE, stainless steel, aluminum, titanium, and combinations thereof.

7. The non-rigid retractor of claim 1, further comprising a second flexible strap including a third anchor for anchoring the second flexible strap to a body part within the incision.

8. The non-rigid retractor of claim 7, wherein the first and second flexible straps are connected to a connection member disposed within the incision that anchors the first and second flexible straps to the body part.

9. The non-rigid retractor of claim 7, wherein the ring is configured to anchor the first and second flexible straps external to the incision.

10. The non-rigid retractor of claim 7, further comprising an adhesive for anchoring external to the incision.

11. The non-rigid retractor of claim 1, further comprising a plurality of flexible straps having anchors for anchoring the straps to a body part within the incision.

12. The non-rigid retractor of claim 1, wherein the first bone anchor comprises a biocompatible anchor.

13. The non-rigid retractor of claim 1, wherein the first bone anchor comprises an intermediate anchor.

14. The non-rigid retractor of claim 1, further comprising an illuminant coupled to the flexible strap for illuminating the surgical site.

15. The non-rigid retractor of claim 1, further comprising an illuminant coupled to the anchor for illuminating the surgical site.

16. An anchoring device for a spinal retractor, comprising;
    an annular ring having a central opening for surrounding an incision for accessing a surgical site;
    a plurality of flexible straps extending from the incision and having anchors for anchoring the plurality of flexible straps to a body part within the incision; and
    anchoring means on the periphery of the annular ring for receiving a portion of the plurality of flexible straps,
    wherein the flexible strap contains therapeutic agents for delivery at the surgical site.

17. The anchoring device of claim 16, wherein the anchoring means comprises a plurality of slots in the annular ring for receiving and retaining a portion of a flexible strap by friction fit.

18. The anchoring device of claim 16, wherein the anchoring means comprises a plurality of clamps for clamping a portion of a flexible strap.

* * * * *